US00PP31004P2

(12) United States Plant Patent
Olesen

(10) Patent No.: US PP31,004 P2
(45) Date of Patent: Nov. 5, 2019

(54) COMPACT FLORIBUNDA ROSE PLANT NAMED 'POULCAS052'

(50) Latin Name: ***Rosa* hybrid**
Varietal Denomination: Poulcas052

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 15/999,578

(22) Filed: Sep. 4, 2018

(51) Int. Cl.
*A01H 5/02* (2018.01)
*A01H 6/74* (2018.01)

(52) U.S. Cl.
USPC ..... Plt./141
CPC ..... *A01H 6/749* (2018.05)

(58) Field of Classification Search
USPC ..... Plt./141
CPC ..... A01H 6/749; A01H 5/02
See application file for complete search history.

*Primary Examiner* — Keith O. Robinson

(57) ABSTRACT

A new garden rose plant of the Compact *Floribunda* class which has abundant, orange red flowers and attractive foliage. This new and distinct variety has shown to be uniform and stable in the resulting generations from asexual propagation.

2 Drawing Sheets

Botanical designation: *Rosa* hybrid.
Variety denomination: 'Poulcas052'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2007 and the resulting seeds were planted in a controlled environment in Fredensborg, Denmark. The new variety, named 'Poulcas052', originated as a single seedling from the stated cross.

The new variety may be distinguished from its male pollen parent and female seed parent primarily by the following characteristics. The male pollen parent plant has red flowers while the new variety has orange red flowers. The female seed parent plant has an arching and spreading habit, while new variety has an upright habit.

The objective of the hybridization of this rose variety was to create a new and distinct variety with unique qualities, such as:

1. Uniform and abundant orange red flowers;
2. Vigorous, but compact growth when propagated on its own roots;
3. Exceptional disease resistance.

This combination of qualities is not present in previously available commercial cultivars of this type, known to the inventor, and distinguish 'Poulcas052' from all other varieties of which we are aware.

As part of the rose development program, Mogens N. Olesen germinated the seeds from the aforementioned hybridization during winter of 2007 and conducted evaluations on the resulting seedlings in a controlled environment in Fredensborg, Denmark. 'Poulcas052' was selected in the spring of 2008 by the inventor as a single plant from the progeny of the aforementioned hybridization.

Asexual reproduction of 'Poulcas052' by rooted cuttings was first done by Mogens N. Olesen in the nursery in Fredensborg, Denmark in July, 2008. This initial and other subsequent asexual propagations conducted in controlled environments have demonstrated that the characteristics of 'Poulcas052' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulcas052'.

Specifically illustrated in FIG. 1 of the drawings are a cluster of open flowers, open flowers at various stages of development, flower buds, flower petals detached, sepals, and reproductive flower parts.

Figure 1:
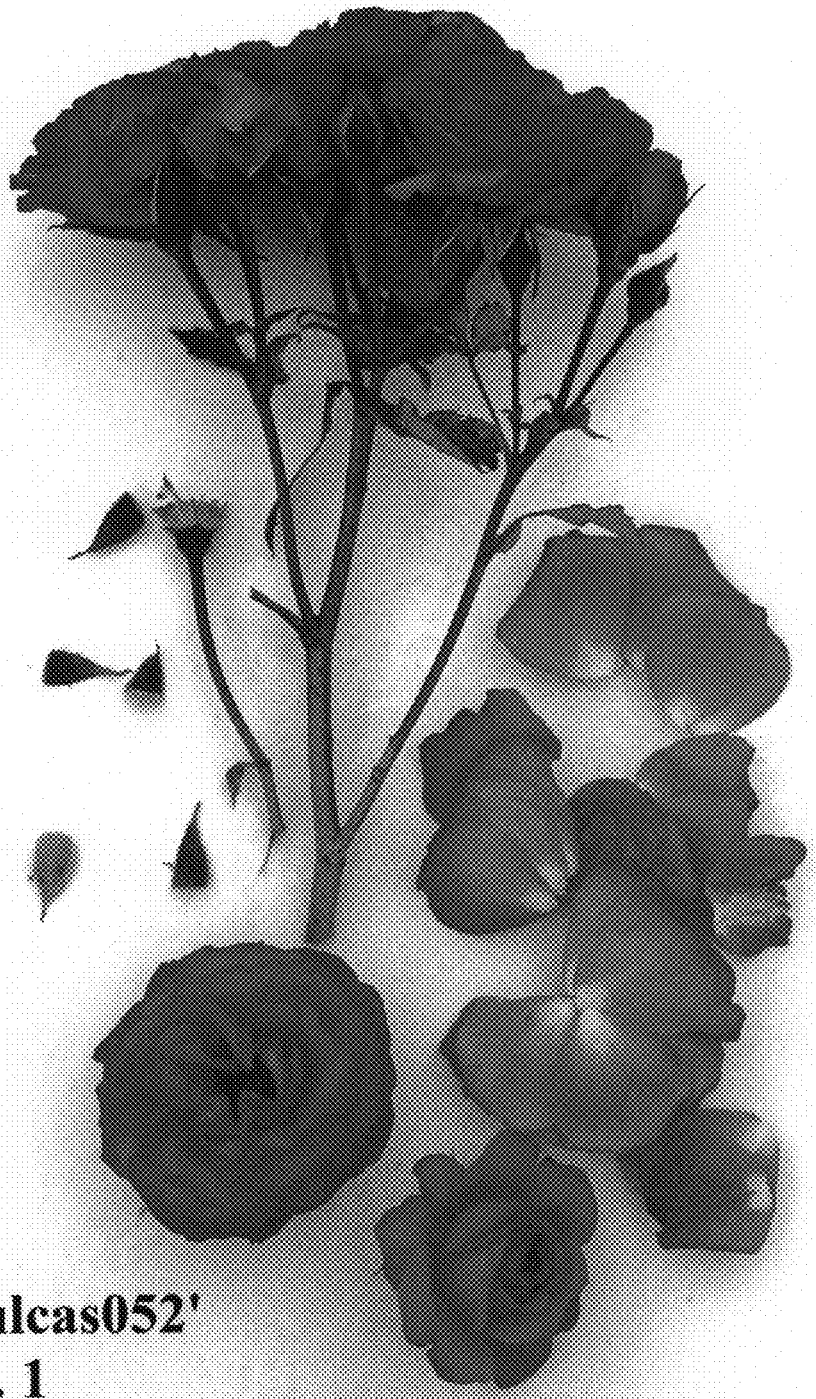
Figure 2:
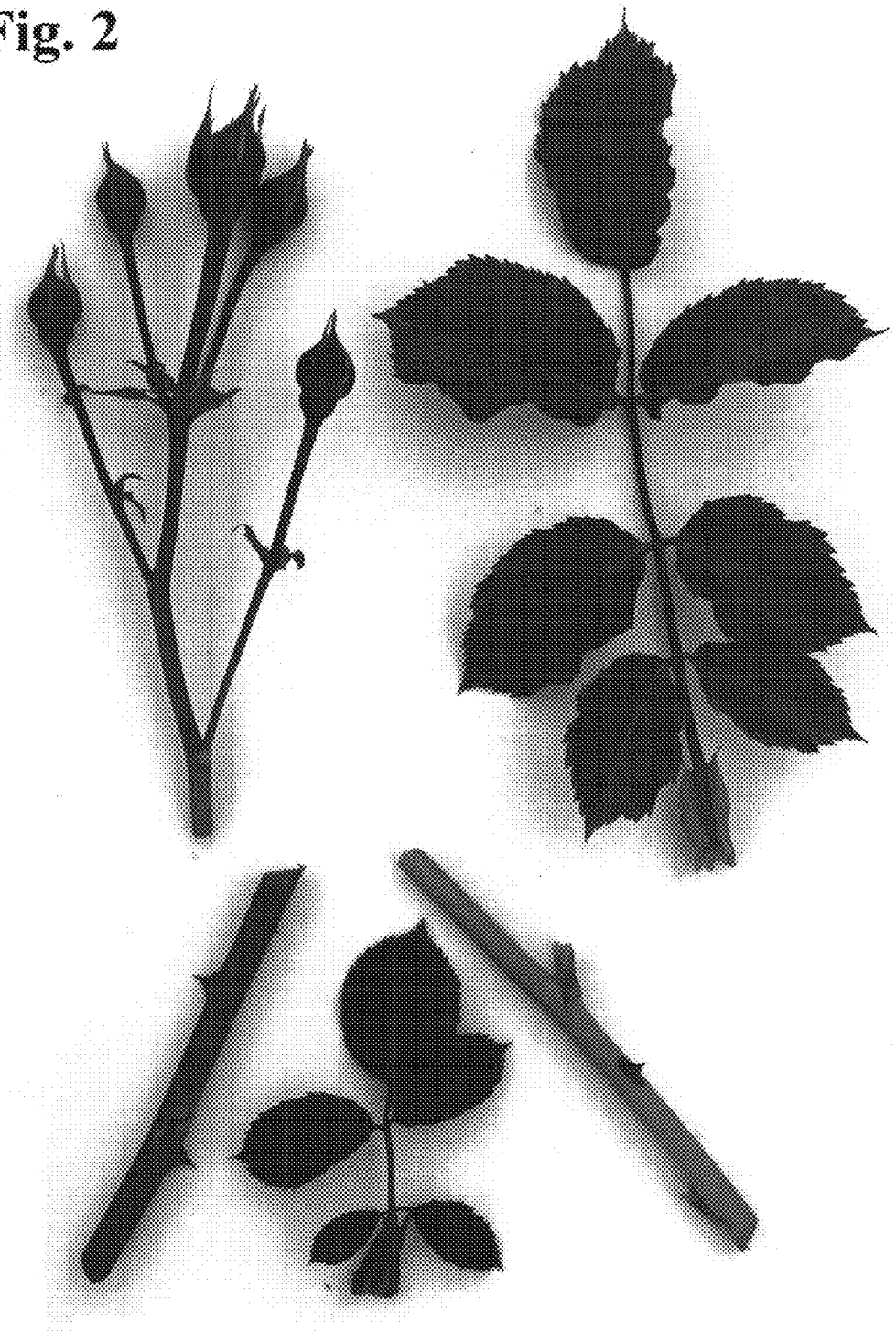

Specifically illustrated in FIG. 2 of the drawings are juvenile and mature leaves, bare stems, and a cluster of flower buds on the branch. Plants shown are 2 years of age.

DETAILED DESCRIPTION OF THE VARIETY

The following is a description of 'Poulcas052', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poulcas034', U.S. Plant Pat. No. 24,225 are compared to 'Poulcas052' in Chart 1.

CHART 1

| | 'Poulcas052' | 'Poulcas034' |
|---|---|---|
| Petal Count | 45 | 70 |
| Flower Diameter | 70-85 mm | 90 to 100 mm |
| General Tonality of Flower Color | Red Group 40A | Red Group 45B |

FLOWER AND FLOWER BUD

Blooming habit: Continuous.

Flower bud:

*Size*.—Upon opening, 30 mm in length from base of receptacle to end of bud. Bud diameter is 19 mm.

*Bud form*.—Ovoid.

*Bud color*.—As sepals divide petals are Red Group 45B.

*Sepal inner surface*.—Color: Green Group 138B, with intonations of Greyed-Red Group 182A. Surface: Lightly pubescent.

*Sepal outer surface*.—Color: Yellow-Green Group 144A, with strong intonations of Greyed-Purple Group 187A. Texture: Smooth.

*Sepal shape*.—Apex: Cirrhose. Base: Flat at union with receptacle.

*Sepal margin*.—Margins have moderate foliaceous appendages on three of the five sepals.

*Sepal size*.—30 mm long, 11 mm wide.

*Receptacle*.—Texture: Smooth. Size: 8 mm in height, 10 mm wide. Color: Yellow-Green Group 144A with strong intonations of Greyed-Purple Group 187A. Shape: Campanulate.

*Pedicel*.—Surface: Rough. Length: 35-45 mm. Diameter: 3 mm on average. Color: Greyed-Red Group 182A with light appearance of Yellow-Green Group 144B. Strength: Strong.

*Peduncle*.—Length: 4 to 8 cm. Diameter: About 5 mm. Color: Yellow-Green Group 144B, with heavy intonations of Greyed-Purple Group 183B. Texture: Smooth.

Flower bud development: Flower buds are borne in clusters of 12 to 15 flower buds per stem. Development as a corymb.

Flower bloom:

*Fragrance*.—Moderate floral scent.

*Duration*.—The blooms have a duration on the plant of approximately 10 days. Petals fall cleanly away from plant after flowers have fully matured.

*Size*.—Flower diameter is 70-85 mm when open. Flower depth is 35 mm.

*Flower shape*.—High centered very double, with a high pointed center which is tightly closed.

*Shape of flower, side view*.—The upper portion is convex, while the lower portion is flat.

Petalage: Under normal conditions, flowers have about 45 petals.

General tonality of flower: Open flowers are Red Group 40A. After flowers mature other intonations appear as Red Group 40C and Red Group 45B.

Petal Color:

*Upon opening and after opening outer and inner petals*.—Upper surface: Red Group 41A with a basal petal spot of Yellow Group 11B. Lower surface: Red Group 52A, with intonations of Red Group 52C. Occasionally a streak of White Group 155A. Basal petal spot Yellow Group 11D.

Petals:

*Petal reflex*.—Moderately reflexed.

*Margin*.—Entire and uniform with occasional clefts. Weak undulations.

*Shape*.—Broad. Apex shape: Rounded. Base shape: Acute.

*Size*.—40 mm (l)×42 mm (w).

*Texture*.—Smooth.

*Thickness*.—Average.

Petaloids:

*Size*.—25 mm (l) by 12 mm (w).

*Quantity*.—5 to 7.

*Shape*.—Elliptical with an acute base and rounded apices.

*Color*.—The upper surface is Red Group 41A with a basal petaloid spot of Yellow Group 11B. The undersurface is Red Group 52A, with intonations of Red Group 52C. Occasionally a streak of White Group 155A. Basal petaloid spot Yellow Group 11D.

Reproductive flower parts:

*Pollen*.—None observed.

*Anthers*.—Size: 4 mm in length. Color: Yellow-Orange Group 16D. Quantity: 45 on average.

*Filaments*.—Color: Yellow Group 11A. Length: 4 mm.

*Pistils*.—Length: 6 mm. Quantity: 30 on average.

*Stigmas*.—Color: Greyed-Yellow Group 160D.

*Styles*.—Color: Yellow-Green Group 154D.

*Location of stigmas*.—Level, in location, relative to the length of the filaments and anthers.

*Hips*.—None Observed.

PLANT

Plant growth: Upright, bushy. Plants are 70 cm in height, and 55 cm wide.

Stems:

*Color of juvenile growth*.—Yellow-Green Group 144B, with intonations of Greyed-Purple Group 183B.

*Color of mature growth*.—Yellow-Green Group 146C.

*Length*.—Canes are about 30 cm from the base of the plant to the flowering portion.

*Diameter*.—About 5 to 8 mm.

*Internodes*.—On mature canes about 35 to 40 mm between nodes.

*Surface texture*.—Young wood: Smooth. Older wood: Smooth.

Prickles: None observed.

Plant foliage:

*Compound leaf*.—180 mm (l)×120 (w).

*Quantity*.—2 leaves per 10 cm of stem on average.

*Leaf bearing angle to the stem*.—45 degrees.

*Color of juvenile foliage*.—Upper side: Yellow-Green Group N144A. Margins Greyed-Purple Group 183A. Lower side: Yellow-Green Group 146C, with intonations of Greyed-Orange Group 176B.

*Color of mature foliage*.—Upper side: Yellow-Green Group 146A. Lower side: Yellow-Green Group 146C.

Plant leaves and leaflets:

*Stipules*.—Size: 30 mm long, 4 mm wide. Quantity: 2 per compound leaf. Shape: Linear, slightly broad based with outward extending apices. Margins: Finely serrated. Color: Yellow-Green Group 144A.

*Petiole*.—Length: 55 mm. Diameter: 1.5 mm. Upper surface color: Greyed-Purple Group 183D. Lower surface color: Yellow-Green Group 144A.

*Rachis*.—Length: 55 mm. Upper surface color: Greyed-Purple Group 183D. Lower surface color: Yellow-Green Group 144A.

*Leaflet*.—Quantity: Normally 7 leaflets. Margins: Serrated. Size: Terminal leaflets are about 70 mm long, 55 mm wide. Shape: Generally elliptical. Base: Rounded. Apex: Cuspidate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

We claim:

1. A new and distinct variety of rose plant of the compact *Floribunda* rose class named 'Poulcas052', substantially as illustrated and described herein, due to its abundant orange red flowers, disease resistance, and extended period of bloom.

* * * * *

'Poulcas052'

'Poulcas052'